United States Patent
Feild

(10) Patent No.: US 6,496,720 B1
(45) Date of Patent: Dec. 17, 2002

(54) PROCESS FOR SENSING AND ANALYZING ELECTRICAL ACTIVITY OF THE HUMAN HEART UTILIZING ONE LEAD SYSTEM WITH AN EGG MONITOR DESIGNED FOR USE WITH ANOTHER LEAD SYSTEM

(75) Inventor: Dirk Q. Feild, Simi Valley, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/493,780

(22) Filed: Jan. 28, 2000

(51) Int. Cl.$^7$ ............................................. A61B 5/0428
(52) U.S. Cl. ...................................................... 600/509
(58) Field of Search ................................ 600/508, 509, 600/512, 522, 523

(56) References Cited

U.S. PATENT DOCUMENTS

| | | |
|---|---|---|
| 3,991,747 A | 11/1976 | Stanly et al. |
| 4,106,495 A | 8/1978 | Kennedy |
| 4,478,223 A | 10/1984 | Allor |
| 4,569,357 A | 2/1986 | Sanz et al. |
| 4,850,370 A | 7/1989 | Dower |
| 5,456,261 A * | 10/1995 | Luczyk ........................ 600/515 |

OTHER PUBLICATIONS

"An Accurate, Clinically Practical System for Spatial Vectorcardiography", by Ernest Frank, Ph.D., Circulation, vol. XIII, May, 1956, pp. 737 to 748.

"On Deriving the Electrocardiogram from Vectorcardio–Graphic Leads", by G.E. Dower, M.D., et al., Clinical Cardiology, vol. 3, Apr. 1980, pp. 87 to 95.

"A Clinical Comparison of Three VCG Lead Systems Using Resistance–Combining Networks", by G.E. Dower, M.B., et al, American Heart Journal, St. Louis, vol. 55, No. 4, Apr., 1958, pp. 523 to 534.

A Lead Synthesizer for the Frank System to Simulate the Standard 12–Lead Electrocardiogram, by Gordon E. Dower, M.B., Journal of Electrocardiology, vol. 1, No. 1, pp. 101 to 116, 1968.

"XYZ Data Interpreted by a 12–Lead Computer Program Using the Derived Electrocardiogram", by Gordon E. Dower, M.B., et al., Journal of Electrocardiology, vol. 12, No. 3, 1979, pp. 249 to 261.

"The ECGD: A Derivation of the ECG from VCG Leads", by Gordon E. Dower, M.D., Journal of Electrocardiology, vol. 17, No. 2, 1984, pp. 189 to 192.

* cited by examiner

Primary Examiner—George R. Evanisko
(74) Attorney, Agent, or Firm—Michael E. Schmitt

(57) ABSTRACT

A process for sensing and analyzing electrical activity of the human heart includes the use of a set of electrodes for a first lead system and an ECG monitor design for use with a second lead system that is different from the first lead system. Output signals from the first lead system electrodes are connected to first, second and third channel inputs for the ECG monitor. The input signals to the ECG monitor are linearly transformed to output first, second and third ECG channels which are consistent with standard output for the first lead system. In linearly transforming the inputted signals to the ECG monitor, differences between the first lead system electrodes and the ECG monitor are manipulated either before the output signals from the first lead system electrodes are fed to the channel inputs for the ECG monitor, or after the ECG monitor has formed channels. Specifically disclosed herein is the transformation of signals between 1) a standard bedside system I lead system, 2) a standard EASI lead system, 3) a standard bedside system II lead system, and 4) a Dower EASI lead system.

21 Claims, 5 Drawing Sheets

PROCESS FOR SENSING AND ANALYZING ELECTRICAL ACTIVITY OF THE HUMAN HEART UTILIZING ONE LEAD SYSTEM WITH AN EGG MONITOR DESIGNED FOR USE WITH ANOTHER LEAD SYSTEM

FIELD OF THE INVENTION

This invention relates to electrophysiology, and to instrumentation and methods for sensing and analyzing activity of the human heart. More specifically, the present invention relates to a process for sensing and analyzing electrical activity of the human heart utilizing one lead system with a three-channel ECG monitor designed for use with a second lead system that is different from the first.

BACKGROUND OF THE INVENTION

Over the last several decades, a variety of diagnostic procedures have been developed for sensing and analyzing activity of the human heart. These include electrocardiography, vectorcardiography and polarcardiography, all of which depend upon related instrumentation used to produce records derived from voltages produced by the heart on the surface of the human body.

The records so produced are graphical in character and require interpretation and analysis to relate the resulting information to the heart condition of the patient or other subject. Historically, such records have been produced directly as visible graphic recordings from wired connections extending from the subject to the recording device. With advances in computer technology, it has become possible to produce such records in the form of digitally stored information for later replication or retrieval and analysis. Likewise, with advances in communication technology, remote (wireless) sensing has become possible.

(a) Electrocardiography

The production of a conventional 12-lead electrocardiogram (ECG) involves the placement of 10 lead electrodes (one of which is a ground or reference electrode) at selected points on the surface of a subject's body. Each electrode acts in combination with one or more other electrodes to detect voltages produced by depolarization and repolarization of individual heart muscle cells. The detected voltages are combined and processed to produce 12 tracings of time varying voltages. The tracings so produced are as follows:

| Lead | Voltage | Lead | Voltage |
| --- | --- | --- | --- |
| I | vL − vR | V1 | v1 − (vR + vL + vF)/3 |
| II | vF − vR | V2 | v2 − (vR + vL + vF)/3 |
| III | vF − vL | V3 | v3 − (vR + vL + vF)/3 |
| aVR | vR − (vL + vF)/2 | V4 | v4 − (vR + vL + vF)/3 |
| aVL | vL − (vR + vF)/2 | V5 | v5 − (vR + vL + vF)/3 |
| aVF | vF − (vL + vR)/2 | V6 | v6 − (vR + vL + vF)/3 | where, in the standard, most widely used system for making short term electrocardiographic recordings of supine subjects, the potentials indicated above, and their associated electrode positions, are:

vL potential of an electrode on the left arm;
vR potential of an electrode on the right arm;
vF potential of an electrode on the left leg;
v1 potential of an electrode on the front chest, right of sternum in the $4^{th}$ rib interspace;
v2 potential of an electrode on the front chest, left of sternum in the $4^{th}$ rib interspace;
v4 potential of an electrode at the left mid-clavicular line in the $5^{th}$ rib interspace;
v3 potential of an electrode midway between the v2 and v4 electrodes;
v6 potential of an electrode at the left mid-axillary line in the $5^{th}$ rib interspace;
v5 potential of an electrode midway between the v4 and v6 electrodes;
vG (not indicated above) is a ground or reference potential with respect to which potentials vL, vR, vF, and v1 through v6 are measured. Typically, though not necessarily, the ground or reference electrode is positioned on the right leg.

Correct interpretation of an ECG requires a great deal of experience since it involves familiarity with a wide range of patterns in the tracings of the various leads. Any ECG which uses an unconventional system of leads necessarily detracts from the body of experience that has been developed, in the interpretations of conventional ECGs, and may therefore be considered generally undesirable. The tracings generated would be understandable only by a relative few who were familiar with the unconventional system.

Nevertheless, other lead systems have evolved from improvements in instrumentation that have permitted extension of electrocardiography to ambulatory, and even vigorously exercising subjects—and to recordings made over hours, or even days. For example, in stress testing the electrodes are moved from the arms to the trunk, although the same number of electrodes (10) are used. The tracings I, II, III, aVR, aVL and aVF are altered by this modification.

Although a 12-lead ECG is considered to be a cost effective heart test, it is to be noted that the relatively large number of electrodes required play an important role in determining costs—not only in terms of the direct cost of the electrodes themselves, but also terms of the time required to properly position and fix each electrode to a subject's body.

(b) Vectorcardiography

The pattern of potential differences on a body surface resulting from electrical activity of the heart can be mathematically approximated by replacing the heart with a dipole equivalent cardiac generator. The magnitude and orientation of this dipole are represented by the heart vector which is continually changing throughout the cycle of the heart beat. The XYZ coordinates of the heart give rise to time varying xyz signals, which may be written out as xyz tracings. Orthogonal leads to give these tracings were developed by Ernest Frank (see *An Accurate, Clinically Practical System For Spatial Vectorcardiography*, Circulation 13: 737, May 1956). Frank experimentally determined the image surface for one individual, and from this proposed a system using seven electrodes on the body, plus a grounding electrode. The conventional letter designations for such electrodes, and their respective positions were:

E at the front midline;
M at the back midline;
I at the right mid-axillary line;
A at the left mid-axillary line;
C at a 45° angle between the front midline and the left mid-axillary line;
F on the left leg;
H on the back of the neck.

The first five electrodes (E, M, I, A and C) were all located at the same transverse level—approximately at the fourth of the fifth rib interspace. A linear combining network of resistors attached to these electrodes gave suitably scaled x, y and z voltage signals as outputs.

Unfortunately, xyz tracings are not as easy to interpret as 12 lead ECGs. However, Frank intended his system for a different purpose: vectorcardiography.

Vectorcardiography abandons the horizontal time coordinate of the ECG in favor of plots or tracings of the orientation and magnitude of the heart vector on each of three planes: a frontal (xy) plane plotting an x-axis (right arm to left arm) against a y-axis (head to foot); a transverse (xz) plane plotting the x-axis against a z-axis (front to back), and a sagittal plane plotting the y-axis against the z-axis.

Although it has long formed a basis for teaching electrocardiography, vectorcardiography has never become widely used. The technique was demanding and the system of electrode placement was different from that required for the ECG. Extra work was required, and it would still be necessary to record a 12-lead ECG separately with a different placement of electrodes.

An alternative to the Frank lead system that required only four active electrodes (R(right arm), A, F, E), and that used a resistor network based on Frank's image surface data was proposed in 1958 by G. E. Dower and J. A. Osborne (see *A Clinical Comparison of Three VCG Lead Systems Using Resistance-Combining Networks*, Am Heart J 55: 523, 1958). However, the xyz signals produced were sometimes different from those of Frank's lead system, and the RAFE system was not adopted.

(c) Polarcardiography

An alternative representation of the heart vector, known as polarcardiography, has been exploited since the early 1960's (see G. E. Dower, *Polarcardiography*, Springfield, Ill, Thomas, 1971). It has certain inherent advantages in defining abnormalities, and forms the basis of a successful program for automated analysis. Based on xyz signals, polarcardiography employs the Frank lead system. In order to render it competitive with the established 12-lead ECG, the lead vector concept has been employed to derive a resistor network that would linearly transform the xyz signals into analogs of the 12-lead ECG signals (see G. E Dower, *A Lead Synthesizer for the Frank Lead System to Stimulate the Standard 12-Lead Electrocardiogram*, J. Electrocardiol 1: 101, 1968, G. E. Dower, H. B. Machado, J. A. Osborne, *On Deriving the Electrocardiogram From Vectorcardiographic Leads*, Clin Cardiol 3: 97, 1980; and G. E. Dower, *The ECGD: A Derivation of the ECG from VCG leads* (editorial), J. Electrocardiol 17: 189, 1984). The ECG thus derived is commonly referred to as the ECGD. Because the ECGD can be acceptable to an interpreting physician, it is not necessary for the technician to apply the electrodes required for a conventional ECG. Further, associated computer facilities can make vectorcardiograms and other useful displays available from the xyz recordings. Nevertheless, the number of electrodes called for by the Frank lead system are required. In addition, the effort required by the technician recording the xyz signals is about the same as for a conventional ECG.

(d) Conventional Three-Channel ECG Monitor and Lead System

More recently, conventional three-channel ECG monitors have been utilized with a four or five wire cable that transmits input from four or five electrodes placed at selected points on the surface of a subject's body. Each electrode acts in combination with one or more other electrodes to detect voltages produced by depolarization and repolarization of individual heart muscle cells. The detected voltages are combined and processed to produce three tracings of time varying voltages. Notably, the three-channel ECG monitor does not act simply as a three-channel amplifier but, rather does some signal manipulation to enable staff to visualize the amplified and displayed or recorded ECG in a conventional manner. More particularly, the three channels of a conventional three-channel ECG bedside monitor do the following:

Channel 1, which is connected as the difference between the left arm electrode voltage and the right arm electrode voltage ($V_{left\ arm}-V_{right\ arm}$) is simply amplified and presented as conventional ECG lead I.

Channel 2, which is connected as the difference between the left leg electrode voltage and the right arm electrode voltage ($V_{left\ leg}-V_{right\ arm}$) is likewise amplified and presented as conventional ECG lead II.

Channel 3, however, is created as the difference between the voltage of an exploring electrode, typically placed on the chest, and the voltage of the "Wilson Central Terminal", a construct intended to represent the voltage at the center of the heart. The Wilson Central Terminal is calculated as the average of the voltages of the electrodes attached to the left arm, right arm and left leg. Hence, $V_{channel3}=V_{chest}-(V_{left\ arm}+V_{right\ arm}+V_{left\ leg})/3$.

If a fifth wire is provided the cable, the electrode is typically attached to the right leg and serves as a ground.

(e) The Dower EASI Lead System

An improved method and apparatus for sensing and analyzing activity of the human heart, and which requires a reduced number of electrodes to produce accurate simulations of conventional twelve-lead electrocardiograms and vectorcardiograms, is described in U.S. Pat. No. 4,850,370 (the contents of which are incorporated herein).

The 4 electrode positions that are fundamental in the use of the Dower lead system consist of electrode position E of the Frank lead system, electrode position A of the Frank lead system, an electrode position S over the upper end of the sternum (manubrium sterni), and electrode position I of the Frank lead system. (Such E, A, S and I electrodes are from time-to-time collectively referred to herein as the "EASI" electrodes.) 12-lead electrocardiographic signals and xyz vectorcardiographic signals can be derived by measuring and, with suitable signal processing means, combining and scaling the voltages present between first, second and third selected pairs of the EASI electrodes.

Sometimes it is desirable to be able to utilize one lead system with an ECG monitor designed for use with a second lead system. For example, it may be desirable at times to utilize a conventional three-channel ECG monitor together with the leads from an EASI lead system or, conversely, utilize a monitor and telemetry system designed for use with EASI leads with conventional leads designed for use with a conventional three-channel monitor. In such cases it is desirable to translate data input from one lead system so that it may be processed through the monitor and telemetry system designed for another lead system. The present invention fulfills these needs and provides other related advantages.

SUMMARY OF THE INVENTION

The present invention provides a novel apparatus for measuring and processing voltages produced by a human heart as sensed between selected points on the surface of a subject's body, and a related process for sensing and analyzing electrical activity of the human heart utilizing a first lead system, with an ECG monitor designed for use with a second lead system. Broadly, the process includes the steps of (1) providing a set of electrodes for a first lead system, 2) providing an ECG monitor designed for use with a second lead system that is different from the first lead system, 3)

connecting output signals from the first lead system electrodes to channel inputs for the ECG monitor, and 4) transforming the inputted signals to the ECG monitor to output at least one channel signal which is consistent with standard output for the first lead system. The transforming step typically involves a linear transformation of the inputted signals to the ECG monitor to output the at least one channel signal. Such linear transformation includes manipulating differences between the first lead system electrodes and the ECG monitor either before the output signals from the first lead system electrodes are fed to the channel inputs for the ECG monitor, or after the ECG monitor has formed channels.

More particularly, the present invention is well suited for use with a first lead system having at least four electrodes attachable to the subject's body at predefined locations, and a three-channel ECG monitor which is designed for use with a second lead system that is different from the first lead system. Examples of lead systems to which the process of the present invention may apply include 1) a standard bedside lead system I, 2) a standard EASI lead system, 3) a standard bedside lead system II, and 4) a Dower EASI lead system.

By way of example, the first lead system may comprise an EASI lead system, and the second lead system may comprise a standard bedside lead system I that includes a conventional three-channel ECG monitor. The first electrode (Elec1) is the E electrode, the second electrode (Elec2) is the S electrode, the third electrode (Elec3) is the A electrode, and the fourth electrode (Elec4) is the I electrode of the EASI lead system. In this case, the first electrode (Elec1) and the second electrode (Elec2) are connected to a first channel (Chan1) of the ECG monitor. The third electrode (Elec3) and the second electrode (Elec2) are connected to a second channel (Chan2) of the ECG monitor. Finally, the fourth electrode (Elec4) is connected to the third channel (Chan3) of the ECG monitor and its input is modified by one-third of the summed input from the first three electrodes (Elec1+Elec2+Elec3).

Similarly, and by way of yet another example, the first lead system may comprise a standard bedside system I lead system that provides input for a conventional three-channel ECG monitor, and the second lead system may comprise a standard EASI lead system. Here, the first electrode (Elec1) is a left arm (LA) electrode, the second electrode (Elec2) is a right arm (RA) electrode, the third electrode (Elec3) is a left leg (LL) electrode, and the fourth electrode is an exploring electrode (typically placed on the chest) of the conventional cable for the conventional three-channel ECG monitor. In such case the first electrode (Elec1) and the second electrode (Elec2) are connected to a first channel (Chan1) of the ECG monitor. The third electrode (Elec3) and the second electrode (Elec2) are connected to a second channel (Chan2) of the ECG monitor. The third electrode (Elec3) and the fourth electrode (Elec4) are then connected to the third channel (Chan3) of the ECG monitor to achieve the desired result.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

By way of background information on the Dower EASI lead system, FIGS. 1, 2, 3 and 4, each depicting a generalized signal processing means or signal processor 100, 200, 300 or 400, as the case may be, serve to illustrate the placement of EASI electrodes on the surface of a subject's body at positions E, A, S and I as hereinbefore described. (In this drawing, the letters E, A, S and I are used not only to identify positions on the human body but also electrodes at such positions.)

The electrodes themselves are common, widely available electrodes used in the process of taking ECGs, VCGs and the like. Their respective positions E, A, S and I serve to avoid the limbs and other undesirable sites such as the C, M and H positions (in the region of the left nipple, the back, and the head or lower neck) as used by Frank. Further, they give good signals with relatively little noise.

Figure 1:
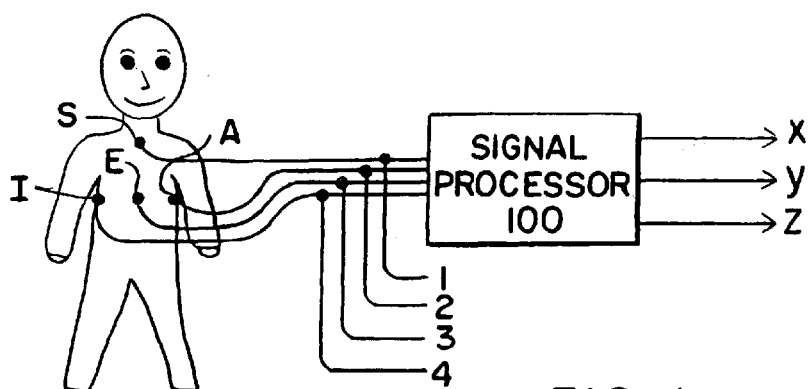
FIG. 1 illustrates the EASI electrode arrangement with signal processing for deriving xyz vectorcardiographic signals.

FIG. 1 illustrates a generalized signal processor 100 receiving EASI electrode signals (via wire connections 1, 2, 3 and 4) as an input, and producing xyz vectorcardiographic signals as an output.

Figure 2:
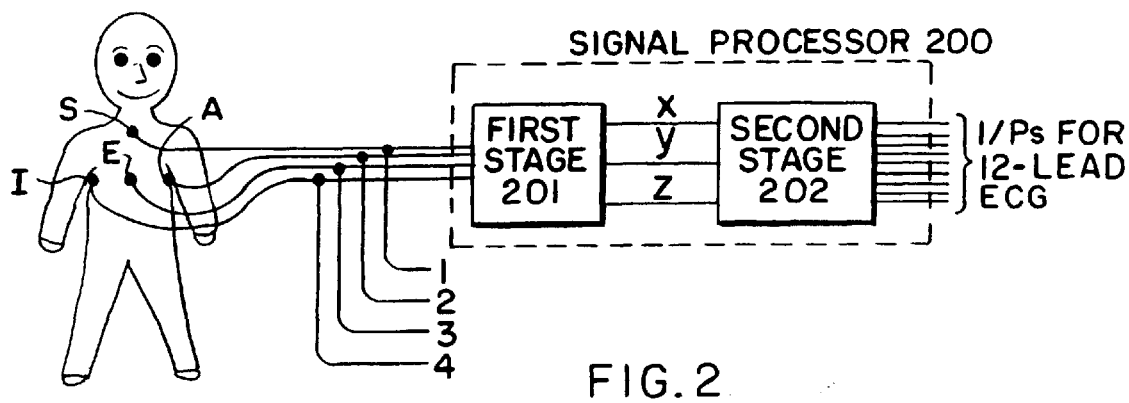
FIG. 2 illustrates the EASI electrode arrangement with signal processing for deriving 12-lead electrocardiographic signals, xyz vectorcardiographic signals being derived at an intermediate stage.

FIG. 2 illustrates a signal processor 200 having a first stage 201 and a second stage 202. In this case, nine output signals are derived to serve as inputs for producing a 12-lead ECG. At the intermediate stage of the output of stage 201 and the input of stage 202, xyz vectorcardiographic are produced. FIG. 2 recognizes that 12-lead electrocardiographic signals may be derived from xyz vectorcardiographic signals. This is of course the basis for the ECGD described above and is not a new observation per se. However, the derivation of 12-lead electrocardiographic signals from derived xyz vectorcardiographic signals produced in the manner indicated through stage 201 in FIG. 2 is considered new by Dower. In principle, it will be noted that there is no fundamental difference between signal processor 100 of FIG. 1 and first stage 201 of signal processor 200 in FIG. 2.

Figure 3:
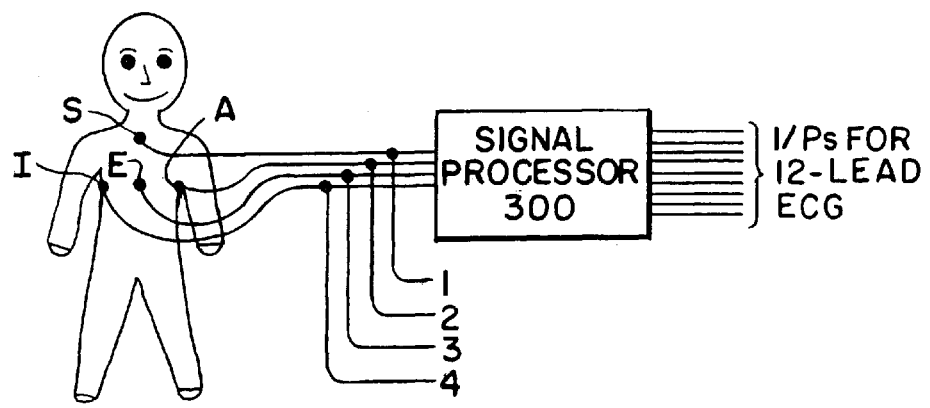
FIG. 3 illustrates the EASI electrode arrangement with signal processing deriving 12-lead electrocardiographic signals.

As will become apparent hereinafter, the signal processing means that are used in the implementation of the Dower lead system comprise linear voltage combining and scaling networks. This is true of signal processor 100 in FIG. 1, and is also true of stages 201 and 202 of signal processor 200 shown in FIG. 2. Given this premise, it will be readily apparent to those skilled in the art that stages 201 and 202 in FIG. 2 may in fact be condensed into a single stage. FIG. 3 highlights the fact that this may be done. Here, signal processor 300 derives 12-lead electrocardiographic signals directly from EASI electrode signal inputs, and there is no necessary production of derived intermediate xyz vectorcardiographic signals as in the case of signal processor 200. Implicitly, signal processor 300 could include such a facility, but it is not essential.

Figure 4:
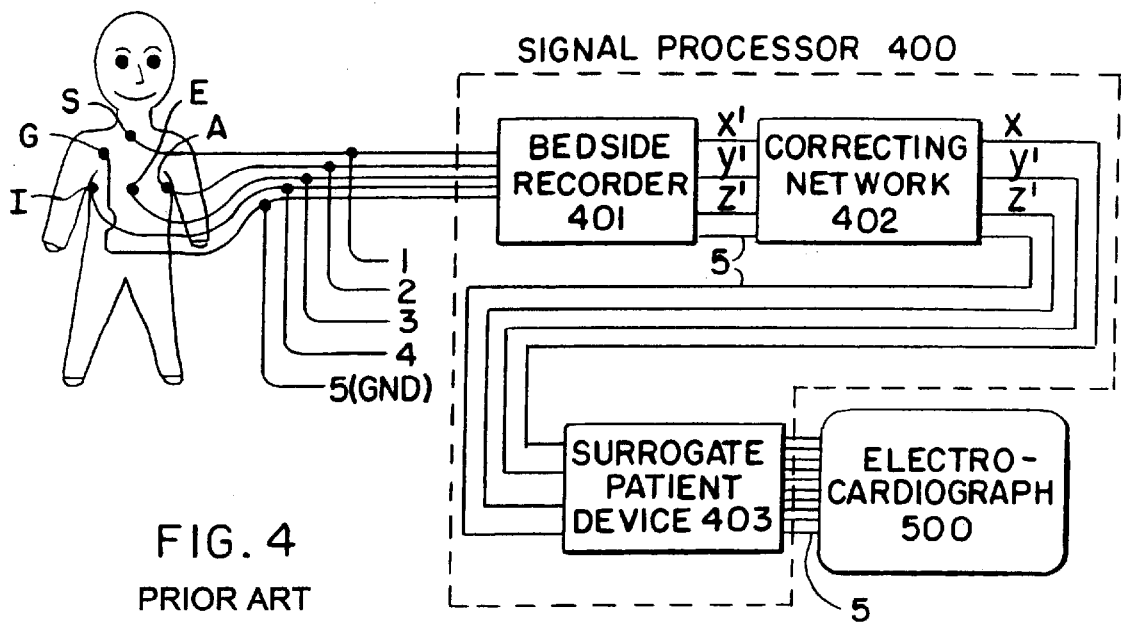
FIG. 4 illustrates in more detail a signal processing means for deriving vectorcardiographic and electrocardiographic signals from EASI electrodes.

FIG. 4, like FIG. 2, shows means for deriving both vectorcardiographic and electrocardiographic signals from EASI electrodes, signal processor 400 of FIG. 4 performing essentially the same function as signal processor 200 of FIG. 2. Additionally, FIG. 4 illustrates connection to an electrocardiograph 500. A fifth or grounding electrode G is also shown in FIG. 4, as is a ground line or path generally designated 5. The placement of grounding electrode G is not critical; it may be placed anywhere convenient—though typically on a subject's chest as indicated in FIG. 4. In any given case, the necessity for a grounding electrode and a ground line will depend on the equipment utilized. FIG. 4 illustrates such elements because they were used in the particular case now to be described in more detail.

Signal processor 400 comprise a bedside recorder 401, a correcting network 402, and a surrogate patient device 403. The combination of recorder 401 and correcting network 402 may be thought of as a first stage 201 in FIG. 2. Surrogate patient device 403 may be thought of as a second stage 202 in FIG. 2. Recorder 401, correcting network 402, and surrogate patient device 403 all act as linear voltage combining and scaling networks.

A preliminary point of note is that bedside recorder 401 and surrogate patient device 403 as stand alone elements are essentially well known devices. The exemplary recorder illustrated is a TOTEMITE™ Bedside Recorder, which embodies a processing network to derive conventional xyz vectorcardiographic signals in accordance with Frank (see above) and which is commonly used to record such signals on magnetic tape. When used in the manner indicated in FIG. 4, signals normally directed to magnetic tape (and which are normally xyz signals) are tapped to provide input signals (x'y'z') for correcting network 402. This is representationally shown in FIG. 5(a) which depicts a Frank network 405 as an included part of bedside recorder 401, but wired at the input to receive four EASI electrode signals. Conventional use of the Frank network is illustrated in FIG. 5(b) which shows each of the network's seven input terminals A, C, E, I, M, H and F present for the purpose of receiving inputs from each of seven corresponding A, C, E, I, M, H and F electrodes (not shown) located at corresponding A, C, E, I, M, H and F positions on a subject (also not shown).

Figure 6:
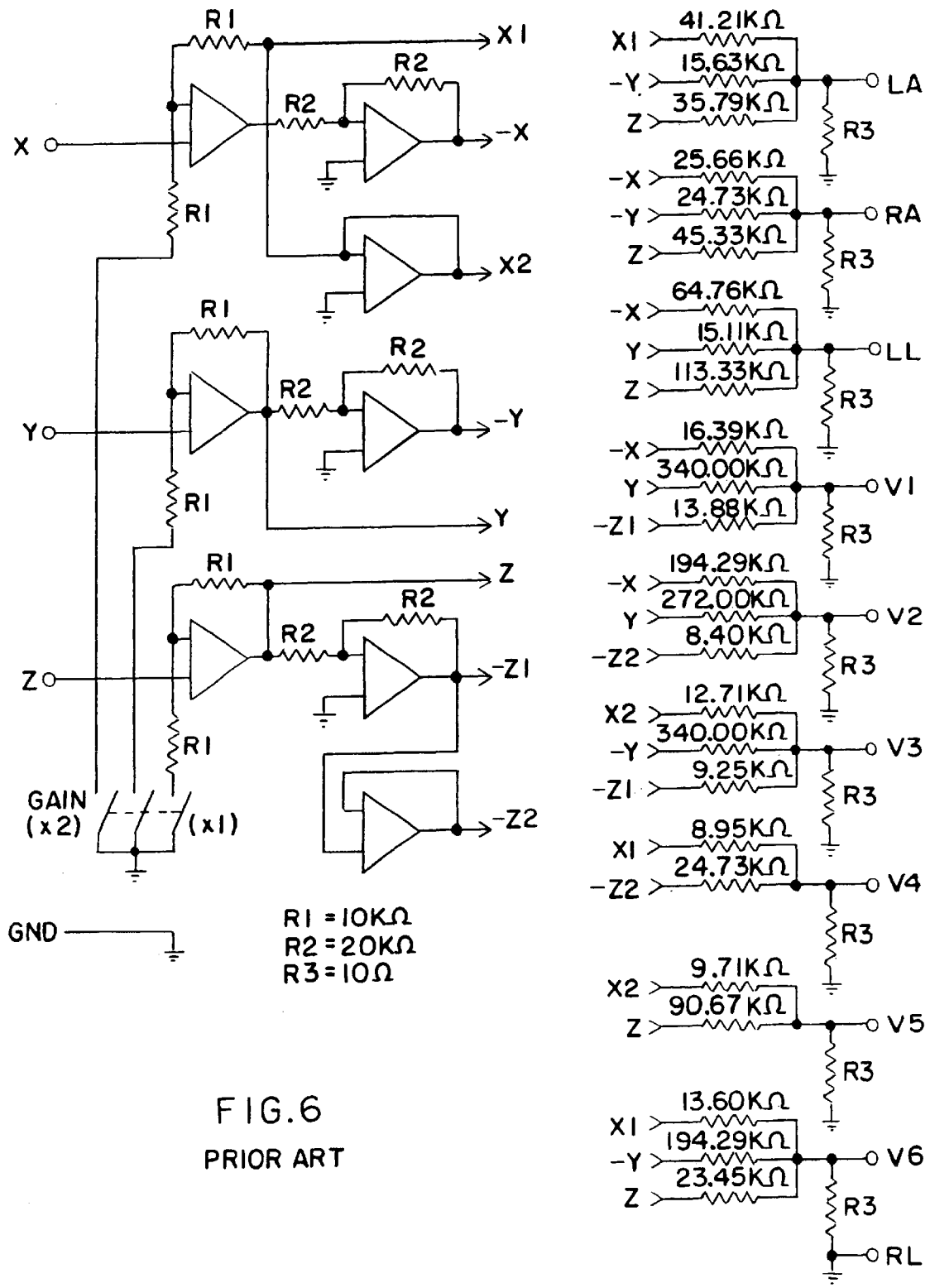
FIG. 6 is a prior art circuit diagram of a surrogate patient device which forms part of the signal processing means in FIG. 4.

Surrogate patient device 403, is a linear processing network whose outputs are scaled to match those that electrocardiographic 500 would "see" from electrodes attached to a subject for a conventional ECG. The design of such networks is known, the result being an ECGD. FIG. 6 illustrates prior art circuitry used to provide the action of a surrogate patient monitor. Since such design is known it will not be described here in any detail. However, it may be noted that the circuit arrangement shown in FIG. 6 is essentially disclosed in *XYZ Data Interpreted by a* 12-*Lead Computer Program Using the Derived Electrocardiogram*, J. Electrocardiol 12: 249, 1979 (by G. E. Dower and H. B. Machado). In that disclosure, signals again taken from a TOTEMITE Bedside Recorder (but using the Frank network forming part of the recorder "normally" to obtain xyz vectorcardiographic signals) were amplified by a factor of 1000 and applied to the XYZ terminal inputs of the surrogate patient device. In the environment shown in FIG. 4, the bedside recorder still receives xyz vectorcardiographic signal inputs; the difference now is that they are not received directly as an amplified output of the bedside recorder, but instead as the output of correcting network 402.

Referring again to FIG. 4 and FIG. 5(a), it can be appreciated that EASI electrode E is connected not only to input E of the Frank network 405, but also input C of the Frank network. Likewise, EASI electrode A is connected not only to input A of the Frank network, but also input M. EASI electrode I is connected not only to input I of the Frank network, but also input F. EASI electrode S is connected to input H of the Frank network. By reason of the departure from the 7 electrodes normally providing input to the Frank network, and by reason of the differing input configuration to the Frank network, it follows naturally that one would not expect the usual xyz vectorcardiographic signals at the output of the network.

More particularly, the conventional input/output signal relationship with a Frank network is:

$$v_x = 0.610 v_A + 0.171 v_C - 0.781 v_I \qquad (1)$$

$$v_y = 0.655 v_F + 0.354 v_M - 1.000 v_H \qquad (2)$$

$$v_z = 0.133 v_A + 0.736 v_M - 0.264 v_I - 0.374 v_E - 0.231 v_C \qquad (3)$$

$V_x$, $V_y$ and $V_z$ appear as potential differences at the three paired outputs of Frank network 500 in FIG. 5(b), $V_A$. $V_C$ and $V_I$, etc. are measured with respect to an arbitrary reference of potential chosen by Frank. Any one of the seven electrodes of the Frank lead system could have been selected as the reference potential.

Figure 5A:
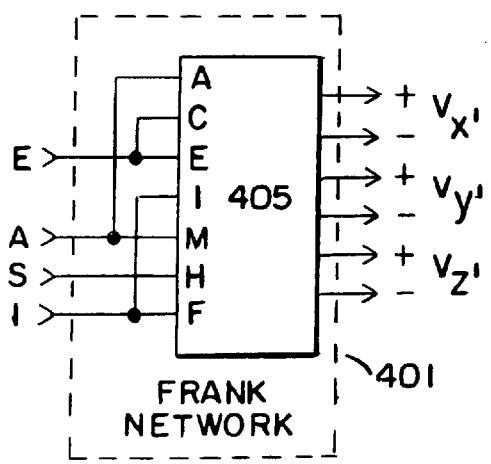
FIG. 5(a) representationally depicts a Frank network forming part of the bedside recorder shown in FIG. 4, the input of such network being configured to receive signals from EASI electrodes in accordance with the present invention.
Figure 5B:
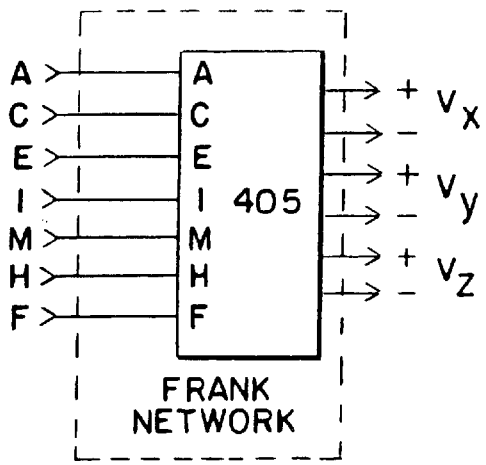
FIG. 5(b) representationally depicts the Frank network as shown in FIG. 5(a), but with a normal (prior art) input configuration to receive signals from conventionally positioned E, M, I, A, C, F and H electrodes as taught by Frank.

When the EASI electrode system is used as the input to the Frank network as shown in FIG. 5(a), the I electrode serves as the reference. (It should be noted that the selection of the I position as the reference is not essential. Any one of the four EASI electrode positions may serve as the reference). With the I position as the reference, there are three input potential differences $V_{AI}$, $V_{EI}$ and $V_{SI}$, as sensed between electrode pairs A-I, E-I and S-I, respectively. The input/output signal relationship of the Frank network with the input configuration modified as shown in FIG. 5(a) becomes:

$$v_x = 0.610 v_{AI} + 0.171 v_{EI}$$

$$v_y = 0.354 v_{AI} - 1.000 v_{SI}$$

$$v_z = 0.869 v_{AI} - 0.605 v_{EI}$$

The signals produced, herein are referred to as x'y'z' signals (illustrated as voltage signals $V_{x'}$, $V_{y'}$ and $V_{z'}$ in FIG. 5(a)), contain sufficient information to derive xyz vectorcardiographic signals. The accessability of this information is enhanced by good signal strengths and low noise ratios associated with the EASI electrode positions on a subject's body.

It is of course key to the Dower system that such information is present and extractable from signals sensed by the EASI electrodes. Also key is the ascertainment of transformation coefficients which enable one to take EASI electrode signals and produce xyz vectorcardiographic and/or electrocardiographic signals. In the case of signal processor 400 shown in FIG. 4, signals x'y'z' essentially act as a "given" and the transformation or "correction" to xyz signals is performed by correcting network 402, the circuit design of which is shown in FIG. 7.

Figure 7:
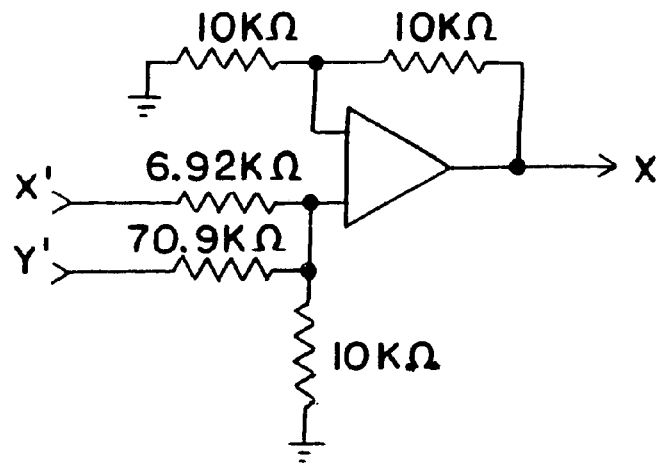
FIG. 7 is a circuit diagram of linear transformation circuits that form correcting network 402.
Figure 7:
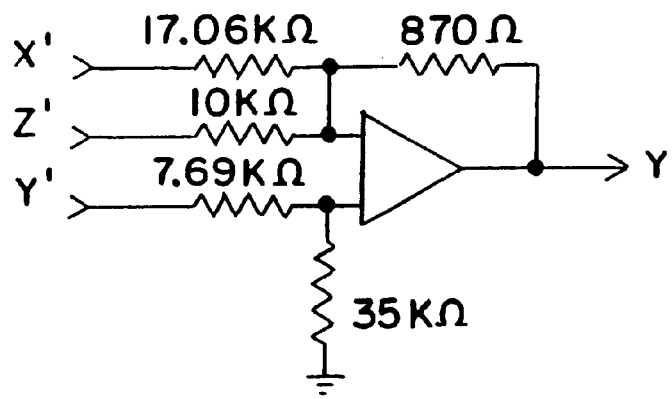
Figure 7:
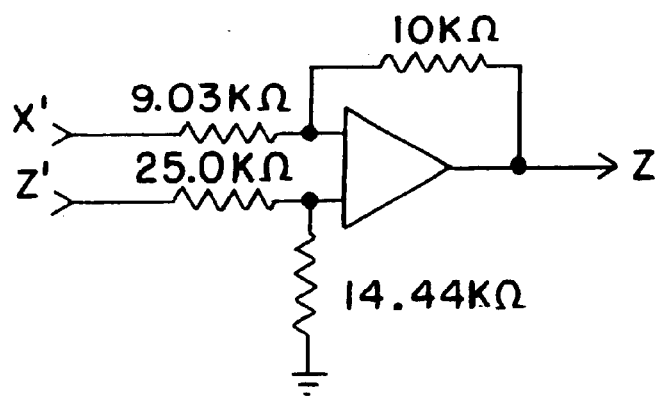

Each of the three circuits shown in FIG. 7, are basic operational amplifier circuits designed to perform linear input/output transformations. As an aside, it should be noted that the input act as voltage sources and are assumed in FIG. 7 to be ideal sources having zero impedance. In practice, this will not be the case. Typically, it will be 100Ω and this value has been assumed as part of the input resistor values shown in FIG. 7. Thus, 100Ω must be subtracted from the resistor values shown in FIG. 7 to obtain the actual resistance values of discrete input resistors.

From the resistor values shown in FIG. 7, it may be readily determined that the three circuits shown will perform to solve the following three equations:

$$v_x = 1.118 v_{x'} + 0.109 v_{z'} \quad (1)$$

$$v_y = -0.051 v_{x'} + 0.933 v_{y'} - 0.087 v_{z'} \quad (2)$$

$$v_z = -1.108 v_{x'} + 0.772 v_{z'} \quad (3)$$

where x, y and z are xyz vectorcardiographic signals. However, implementation does not start with the foregoing equations or with the equation solving circuits shown in FIG. 1; it starts with a determination of what the coefficients in the foregoing equations should be, and then proceeds with the routine design of circuitry which operates to solve the equations.

A statistical method of determining such coefficients has been devised, and has been found to work remarkably well. Both x'y'z' and xyz signals are sampled at corresponding times from a number of subjects. With the aid of a computer, the samples may be compared using standard least-square methods to extract correlating coefficients. The resulting equations express x, y and z in terms of x', y' and z'.

Because the application of electrodes for stress testing requires careful preparation of the skin, and because the electrodes are used only once, the requirement of only five EASI electrodes (including a ground electrode), connected instead of the ten normally needed, results in a saving of time and money. Furthermore, by reason of their location favoring large signals and relatively small amounts of movement artifact or signal noise, the quality of the tracings obtained tends to be improved. These benefits can be obtained without modification to existing equipment. However, it will be appreciated that with suitable equipment a variety of displays (including vectorcardiography and polarcardiography) becomes obtainable from xyz signals without modifying the recording technique—the record in all cases being taken from EASI electrode positions.

It will also be apparent to those skilled in the art that the discrete elements represented by Frank network 405 in FIG. 5(*a*) and the active resistive circuits shown in FIG. 7 can be condensed to provide a more direct derivation of xyz signals from the EASI electrode signals which are the input to network 402. This would forego the immediate advantage of utilizing a commercially available recorder, but recognized that the overall network can readily be condensed and embodied in a single patient's cable. The same is true if one extends the process to include circuitry of surrogate patient device 403.

It is sometimes desirable to utilize EASI electrode signals with a conventional three-channel monitor/recorder or, inversely, utilize an EASI monitor/recorder with conventional electrodes. In other words, an apparatus and process is needed which permits the sensing and analyzing of electrical activity of the human heart utilizing a first lead system, with an ECG monitor designed for use with a second lead system that is different from the first lead system.

Figure 8:
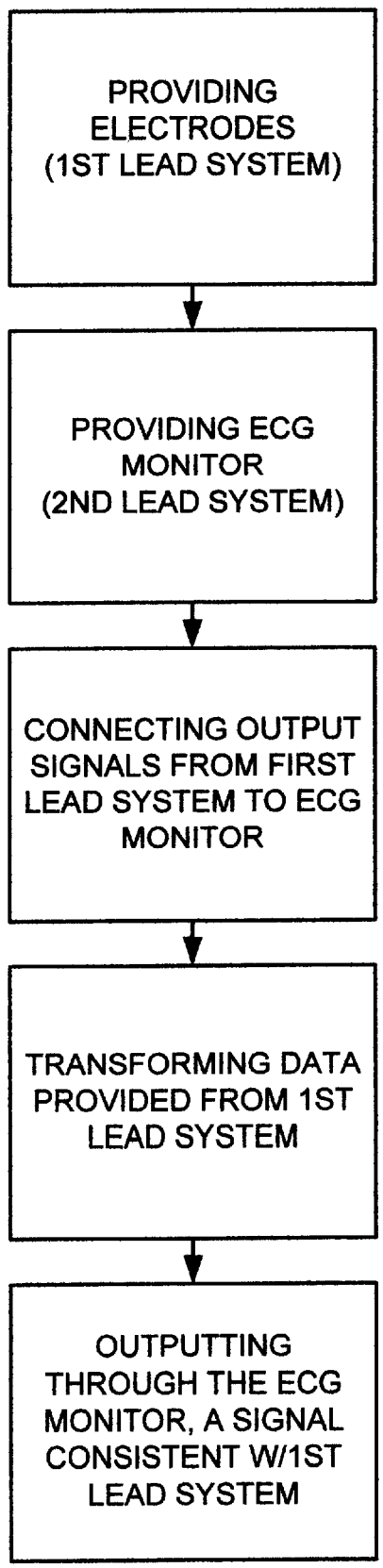
FIG. 8 is a flowchart of a process in accordance with the present invention.

The following description of processes in accordance with the present invention is to be read with reference to FIG. 8.

In accordance with the present invention, a process for sensing and analyzing electrical activity of the human heart is provided which comprises the steps of (1) providing a set of electrodes for a first lead system, (2) providing an ECG monitor designed for use with a second lead system that is different from the first lead system, (3) connecting output signals from the first lead system electrodes to channel inputs for the ECG monitor, and (4) transforming the inputted signals to the ECG monitor to output at least one channel signal which is consistent with standard output for the first lead system. As will be noted below in more detail, the transforming step includes a linear transformation of the inputted signals to the ECG monitor to output the at least one channel signal. Such includes manipulating differences between the first lead system electrodes and the ECG monitor either after the ECG monitor has formed channels or before the output signals from the first lead system electrodes are fed to the channel inputs for the ECG monitor.

In order to fully illustrate advantages to be realized by the present invention, its application to use with four exemplary lead systems will be illustrated below. More particularly, in the examples below either the first or second lead system may comprise one of the following: (1) a standard bedside system I lead system, (2) a standard EASI lead system, (3) a standard bedside system II lead system, and (4) a Dower EASI lead system.

Four Example Lead Systems

Lead System 1: Standard bedside system I giving leads I, II and one V lead

Lead System 2: Standard EASI system

Lead System 3: Standard bedside system II giving leads II, III, and one V lead

Lead System 4: Dower EASI system

| Lead System 1 | | |
|---|---|---|
| Electrode Positions | Channel Input | Result |
| Elec1 = LA | Chan1 = Elec1 − Elec2 | Chan1 = LA − RA |
| Elec2 = RA | Chan2 = Elec3 − Elec2 | Chan2 = LL − RA |
| Elec3 = LL | Chan3 = Elec4 − W | Chan3 = Cx − W |
| Elec4 = Cx* | W = (Elec1 + Elec2 + Elec3)/3 | |

*Cx denotes the unipolar lead that leads to the binolar Vx lead.

| Lead System 2 | | |
|---|---|---|
| Electrode Positions | Channel Input | Result |
| Elec1 = E | Chan1 = Elec1 − Elec2 | Chan1 = E − S |
| Elec2 = S | Chan2 = Elec3 − Elec2 | Chan2 = A − S |
| Elec3 = A | Chan3 = Elec3 − Elec4 | Chan3 = A − I |
| Elec4 = I | | |

| Lead System 3 | | |
|---|---|---|
| Electrode Positions | Channel Input | Result |
| Elec1 = LA | Chan1 = Elec3 − Elec2 | Chan1 = LL − RA |
| Elec2 = RA | Chan2 = Elec3 − Elec1 | Chan2 = LL − LA |
| Elec3 = LL | Chan3 = W − Elec4 | Chan3 = W − Cx |
| Elec4 = Cx | W = (Elec1 + Elec2 + Elec3)/3 | |

| Lead System 4 | | |
|---|---|---|
| Electrode Positions | Channel Input | Result |
| Elec1 = E | Chan1 = Elec1 − Elec2 | Chan1 = E − I |
| Elec2 = I | Chan2 = Elec3 − Elec2 | Chan2 = A − I |
| Elec3 = A | Chan3 = Elec4 − Elec2 | Chan3 = S − I |
| Elec4 = S | | |

As set forth above, in the lead system No. 1 (standard bedside system I giving leads I, II, and IV lead), the first electrode (Elec1) is attached to the left arm (LA), the second electrode (Elec2) is attached to the right arm (RA), the third electrode (Elec3) is attached to the subject's left leg (LL), and the fourth electrode (Elec4) is an exploring electrode of the conventional cable, and comprises a unipolar lead that leads to the bipolar Vx lead. As illustrated in the table above, the first and second electrodes (Elec1 and Elec2) are connected to the first channel (Chan1) of the ECG monitor. Similarly, the second and third electrodes (Elec2 and Elec3) are connected to the second channel (Chan2) of the ECG monitor. The fourth electrode (Elec4) is connected to the third channel (Chan3) of the ECG monitor together with a W input which comprises a summation of the voltages from the first through third electrodes (Elec1+Elec2+Elec3) divided by 3.

With further reference to chart above, the lead system 2 is a standard EASI system wherein first electrode (Elec1) is the E electrode, the second electrode (Elec2) is the S electrode, the third electrode (Elec3) is the A electrode, and the fourth electrode (Elec4) is the I electrode of the EASI lead system. Here, the first and second electrodes (Elec1 and Elec2) are attached to the first channel (Chan1) to provide the E-S lead. Similarly, the third and second electrodes (Elec3 and Elec2) are connected to the second channel (Chan2) to give the A-S lead. Finally, the third electrode and the fourth electrode (Elec3 and Elec4) are connected to the third channel (Chan3) to provide the A-I lead.

With the foregoing in mind, the electrode positions, channel input and results for a lead system 3 and lead system 4, illustrated above, is self explanatory.

One exemplary embodiment of the invention involves utilizing the standard EASI system (lead system 2) in an environment that already has conventional three-channel ECG monitoring equipment (lead system 1). At first blush the problem may seem trivial, but it is not because the conventional three-channel ECG monitor does not act simply as a three-channel amplifier but, rather does some signal manipulation to enable the staff to visualize the amplified and displayed or recorded ECG in a conventional manner. This particular exemplary embodiment is illustrated in the table below:

Using Lead System 1 in Lead System 2 positions (EASI from Standard I)

| Electrode Positions | Channel Input | Result |
|---|---|---|
| Elec1 = E | Chan1 = Elec1 − Elec2 | Chan1 = E − S |
| Elec2 = S | Chan2 = Elec3 − Elec2 | Chan2 = A − S |
| Elec3 = A | Chan3 = Ele4 − W | Chan3 = I − W |
| Elec4 = I | W = (1/3)(Elec1 + Elec2 + Elec3) | |

Pre Processing Function
  G(Elec1)=Elec1
  G(Elec2)=Elec2
  G(Elec3)=Elec3
  G(Elec4)=+(1/3)Elec1+(1/3)Elec2+(4/3)Elec3−Elec4
Pre Processing Function then Lead System 1 gives Lead System 2
  E-S
  A-S
  (1/3)E+(1/3)S+(4/3)A-I−(1/3)E−(1/3)S−(1/3)A=A-I
Post Processing Function
  F(Chan1)=Chan1
  F(Chan2)=Chan2
  F(Chan3)=−(1/3)Chan1+(2/3)Chan2−Chan3
Lead System 1 then Post Processing Function gives Lead System 2
  E-S
  A-S
  −(1/3)E+(1/3)S+(2/3)A−(2/3)S-I+(1/3)E+(1/3)S+(1/3)A= A-I As shown above, the first electrode (Elec1) is the E electrode, the second electrode (Elec2) is S electrode, the third electrode (Elec3) is the A electrode, and the fourth electrode (Elec4) is the I electrode of the EASI system. The first and second electrodes (Elec1 and Elec2) are connected to the first channel (Chan1) to provide the E-S input, the second and third electrodes (Elec2 and Elec3) are connected to the second channel (Chan2) to provide the A-S input, and the fourth electrode (Elec4) and the W composite of the first through third electrodes are connected to channel three (Chan3) to provide an I-W lead.

As mentioned previously, the transforming step includes the step of manipulating differences between the first lead system electrodes (EASI electrodes) and the ECG monitor (of the lead system 1) before the output signals from the first lead system electrodes are fed into the channel inputs for the ECG monitor. This is known as the "pre processing function" shown above. Similarly, the transforming step may include the step of manipulating differences between the first lead system electrodes and the ECG monitor after the ECG monitor has formed channels. This is known as the "post processing function" illustrated above.

Notably, the I-W lead to channel three (Chan3) is essentially a linear manipulation of data provided by all four electrodes to provide the A-I lead of a standard EASI system. The calculations shown above in both the "pre processing function" and the "post processing function" simply "undo" the arithmetic modifications that are done internally within the conventional bedside monitor and thus allow the retrofitting of the standard EASI system (lead system 2) to the conventional three-channel bedside monitors already in the field (lead system 1) without any modifications to the monitors themselves and only adding some very simple processing into the EASI algorithm. Indeed, since the pre processor and EASI algorithm are both linear operations, in practice it can be collapsed into a single operation.

With an understanding of the foregoing example, several additional examples of application of the invention will be illustrated below. The first example illustrated involves use of the ECG monitor from a standard EASI system (lead system 2) with electrodes from a standard bedside system I lead system (lead system 1).

Using Lead System 2 in Lead System 1 positions (Standard I from EASI)

| Electrode Positions | Channel Input | Result |
|---|---|---|
| Elec1 LA | Chan1 = Elec1 − Elec2 | Chan1 = LA − RA |
| Elec2 RA | Chan2 = Elec3 − Elec2 | Chan2 = LL − RA |
| Elec3 = LL | Chan3 = Elec3 − Elec4 | Chan3 = LL − Cx |
| Elec4 = Cx | | |

Pre Processing Function
   $G(Elec1)=Elec1$
   $G(Elec2)=Elec2$
   $G(Elec3)=Elec3$
   $G(Elec4)=+(1/3)Elec1+(1/3)Elec2+(4/3)Elec3-Elec4$ Pre Processing Function then Lead System 1 gives Lead System 2
   LA-RA
   LL-RA
   $LL-(1/3)LA-(1/3)RA-(4/3)LL+Cx=Cx-(1/3)(LA+RA+LL)$ Post Processing Function
   $F(Chan1)=Chan1$
   $F(Chan2)=Chan2$
   $F(Chan3)=-(1/3)Chan1+(2/3)Chan2-Chan3$ Lead System 1 then Post Processing Function gives Lead System 2
   LA-RA
   LL-RA
   $-(1/3)LA+(1/3)RA+(2/3)LL-(2/3)RA-LL+Cx=Cx-(1/3)(LA+RA+LL)$ The next table illustrates the use of a standard three-channel ECG monitor from the standard bedside system I lead system (lead system 1) in a Dower EASI system (lead system 4).

Using Lead System 1 in Lead System 4 positions (Dower from Standard I)

| Electrode Positions | Channel Input | Result |
|---|---|---|
| Elec1 = E | Chan1 = Elec1 − Elec2 | Chan1 = E − S |
| Elec2 = S | Chan2 = Elec3 − Elec2 | Chan2 = A − S |
| Elec3 = A | Chan3 = Elec4 − W | Chan3 = I − W |
| Elec4 = I | W = (Elec1 + Elec2 + Elec3)/3 | |

Pre Processing Function
   $G(Elec1)=Elec1$
   $G(Elec2)=Elec4$
   $G(Elec3)=Elec3$
   $G(Elec4)=+(1/3)Elec1+Elec2+(1/3)Elec3-(2/3)Elec4$ Pre Processing Function then Lead System 1 gives Lead System 4
   E-I
   A-I
   $(1/3)E+S+(1/3)A-(2/3)I-(1/3)E-(1/3)I-(1/3)A=S-I$ Post Processing Function
   $F(Chan1)=+(2/3)Chan1-(1/3)Chan2-Chan3$
   $F(Chan2)=-(1/3)Chan1+(2/3)Chan2-Chan3$
   $F(Chan3)=-(1/3)Chan1-(1/3)Chan2-Chan3$ Lead System 1 then Post Processing Function gives Lead System 4
   $+(2/3)E-(2/3)S-(1/3)A+(1/3)S-I+(1/3)E+(1/3)S+(1/3)A=E-I$
   $-(1/3)E+(1/3)S+(2/3)A-(2/3)S-I+(1/3)E+(1/3)S+(1/3)A=A-I$
   $-(1/3)E+(1/3)S-(1/3)A+(1/3)S-I+(1/3)E+(1/3)S+(1/3)A=S-I$ The next illustration involves utilizing the ECG monitor from the Dower EASI lead system (lead system 4) with electrodes from the standard bedside system I (lead system 1).

Using Lead System 4 in Lead System I positions (Standard I from Dower)

| Electrode Positions | Channel Input | Result |
|---|---|---|
| Elec1 = LA | Chan1 = Elec1 − Elec2 | Chan1 = LA − RA |
| Elec2 = RA | Chan2 = Elec3 − Elec2 | Chan2 = LL − RA |
| Elec3 = LL | Chan3 = Elec4 − Elec2 | Chan3 = Cx − RA |
| Elec4 = Cx | | |

Pre Processing Function
   $G(Elec1)=Elec1$
   $G(Elec2)=Elec4$
   $G(Elec3)=Elec3$
   $G(Elec4)=+(1/3)Elec1+Elec2+(1/3)Elec3-(2/3)Elec4$ Pre Processing Function then Lead System 1 gives Lead System 4
   E-I
   A-I
   $(1/3)E+S+(1/3)A-(2/3)I-(1/3)E-(1/3)I-(1/3)A=S-I$ Post Processing Function
   $F(Chan1)=+(2/3)Chan1-(1/3)Chan2-Chan3$
   $F(Chan2)=-(1/3)Chan1+(2/3)Chan2-Chan3$
   $F(Chan3)=-(1/3)Chan1-(1/3)Chan2-Chan3$ Lead System 1 then Post Processing Function gives Lead System 4
   $+(2/3)E-(2/3)S-(1/3)A+(1/3)S-I+(1/3)E+(1/3)S+(1/3)A=E-I$
   $-(1/3)E+(1/3)S+(2/3)A-(213)S-I+(1/3)E+(1/3)S+(1/3)A=A-I$
   $-(1/3)E+(1/3)S-(1/3)A+(1/3)S-I+(1/3)E+(1/3)S+(1/3)A=S-I$ The following table illustrates using the ECG monitor from a standard bedside system II (lead system 3) with electrodes from a standard EASI system (lead system 2).

Using Lead System 3 in Lead System 2 positions (EASI from Standard II)

| Electrode Positions | Channel Input | Result |
|---|---|---|
| Elec1 = S | Chan1 = Elec3 − Elec2 | Chan1 = A − I |
| Elec2 = I | Chan2 = Elec3 − Elec1 | Chan2 = A − S |
| Elec3 = A | Chan3 = W − Elec4 | Chan3 = W − E |
| Elec4 = E | W = (1/3)(Elec1 + Elec2 + | |

-continued

| Electrode Positions | Channel Input | Result |
|---|---|---|
| | Elec3) | |

Pre Processing Function
    G(Elec1)=−Elec4
    G(Elec2)=−Elec3
    G(Elec3)=−Elec1
    G(Elec4)=−(1/3)Elec1+Elec2−(4/3)Elec3−(1/3)Elec4
Pre Processing Function then Lead System 3 gives Lead System 2
    −S+E
    −S+A
    −(1/3)E−(1/3)A−(1/3)S+(1/3)S-I+(4/3)A+(1/3)E=A-I
Post Processing Function
    F(Chan1)=−(1/3)Chan1+(2/3)Chan2−Chan3
    F(Chan2)=+Chan2
    F(Chan3)=+Chan1
Lead System 3 then Post Processing Function gives Lead System 2
    −(1/3)A+(1/3)I+(2/3)A−(2/3)S−(1/3)S−(1/3)I−(1/3)A+E=E-S
    A-S
    A-I The following table illustrates the use of a monitor from a standard EASI lead system (lead system 2) with electrodes from a standard bedside system II (lead system 3).

Using Lead System 2 in Lead System 3 positions (Standard II from EASI)

| Electrode Positions | Channel Input | Result |
|---|---|---|
| Elec1 = LA | Chan1 = Elec1 − Elec2 | Chan1 = LA − RA |
| Elec2 = RA | Chan2 = Elec3 − Elec2 | Chan2 = LL − RA |
| Elec3 = LL | Chan3 = Elec3 − Elec4 | Chan3 = LL − Cx |
| Elec4 = Cx | | |

Pre Processing Function
    G(Elec1)=Elec3
    G(Elec2)=Elec2
    G(Elec3)=−Elec1+Elec2+Elec3
    G(Elec4)=−(2/3)Elec1−(2/3)Elec2+(4/3)Elec3−Elec4
Pre Processing Function then Lead System 2 gives Lead System 3
    LL−RA
    −LA+RA+LL−RA=LL−LA
    −LA+RA+LL+(2/3)LA+(2/3)RA−(4/3)LL−Cx=(1/3)(LA+RA+LL)−Cx
Post Processing Function
    F(Chan1)=+Chan2
    F(Chan2)=−Chan1+Chan2
    F(Chan3)=+(1/3)Chan1−(2/3)Chan2+Chan3
Lead System 2 then Post Processing Function gives Lead System 3
    LL−RA
    −LA+RA+LL−RA=LL−LA
    (1/3)LA−(1/3)RA−(2/3)LL+(2/3)RA+LL−Cx=(1/3)(LA+RA+LL)−x−Cx The following table illustrates use of a monitor from the Dower EASI lead system (lead system 4) with electrodes from a standard bedside system II (lead system 3).

Using Lead System 4 in Lead System 3 positions (Standard II from Dower)

| Electrode Positions | Channel Input | Result |
|---|---|---|
| Elec1 = LA | Chan1 = Elec1 − Elec2 | Chan1 = LA − RA |
| Elec2 = RA | Chan2 = Elec3 − Elec2 | Chan2 = LL − RA |
| Elec3 = LL | Chan3 = Elec4 − Elec2 | Chan3 = Cx − RA |
| Elec4 = Cx | | |

Pre Processing Function
    G(Elec1)=Elec3
    G(Elec2)=Elec2
    G(Elec3)=−Elec1+Elec2+Elec3
    G(Elec4)=+(1/3)Elec1+(4/3)Elec2+(1/3)Elec3−Elec4
Pre Processing Function then Lead System 2 gives Lead System 3
    LL−RA
    −LA+RA+LL−RA=LL−LA
    +(1/3)LA+(4/3)RA+(1/3)LL−Cx−RA=(1/3)(LA+RA+LL)−Cx
Post Processing Function
    F(Chan1)=+Chan2
    F(Chan2)=−Chan1+Chan2
    F(Chan3)=+(1/3)Chan1+(1/3)Chan2+Chan3
Lead System 2 then Post Processing Function gives Lead System 3
    LL−RA
    −LA+RA+LL−RA=LL−LA
    (1/3)LA−(1/3)RA+(1/3)LL−(1/3)RA−Cx+RA=(1/3)(LA+RA+LL)−Cx Finally, the following table illustrates use of a monitor from a standard bedside system II (lead system 3) with electrodes from the Dower EASI lead system (lead system 4).

Using Lead System 3 in Lead System 4 positions (Dower from Standard II)

| Electrode Positions | Channel Input | Result |
|---|---|---|
| Elec1 = S | Chan1 = Elec3 − Elec2 | Chan1 = A − I |
| Elec2 = I | Chan2 = Elec3 − Elec1 | Chan2 = A − S |
| Elec3 = A | Chan3 = W − Elec4 | Chan3 = W − E |
| Elec4 = E | W = (1/3)(Elec1 + Elec2 + Elec3) | |

Pre Processing Function
    G(Elec1)=+Elec2
    G(Elec2)=+Elec2+Elec3−Elec4
    G(Elec3)=+Elec3
    G(Elec4)=−Elec1+(5/3)Elec2−Elec3+(4/3)Elec4
Pre Processing Function then Lead System 3 gives Lead System 2
    A-I−A+E=E-I
    A-I
    (1/3)(I+I+A−E+A)−(−S+(5/3)(I+A−E)−A+(4/3)E)=S-I
Post Processing Function
    F(Chan1)=+(2/3)Chan1−(1/3)Chan2−Chan3
    F(Chan2)+Chan1
    F(Chan3)=+Chan1−Chan2

Lead System 3 then Post Processing Function gives Lead System 2

+(2/3)A−(2/3)I−(1/3)A+(1/3)S−(1/3)S−(1/3)I−(1/3)A+E=E-I

A-I

A-I−A+S=S-I

Although several embodiments of the invention have been described in detail for purposes of illustration, various modifications of each may be made without departing from the spirit and scope of the invention. Accordingly, the invention is not to be limited, except as by the appended claims.

I claim:

1. A process for sensing and analyzing electrical activity of a human heart, comprising the steps of:
   providing a set of electrodes designed for a first lead system;
   providing an ECG monitor designed to receive output signals from a second lead system that is different from the first lead system, and form output channels consistent with output for which the second lead system was designed;
   connecting output signals from the first lead system electrodes to channel inputs for the ECG monitor;
   transforming data provided by the output signals from the first lead system; and
   outputting through the ECG monitor at least one channel signal which is consistent with output for which the first lead system was designed.

2. The process of claim 1, wherein the transforming step includes a linear transformation of the data to output the at least one channel signal.

3. The process of claim 1, wherein the transforming step includes the step of applying an algorithm to the data after the ECG monitor has formed channels.

4. The process of claim 1, wherein the transforming step includes the step of applying an algorithm to the data before the output signals from the first lead system electrodes are fed to the channel inputs for the ECG monitor.

5. The process of claim 1, wherein the transforming step includes the step of transforming the data to the ECG monitor to output first, second and third ECG channels which are consistent with output for which the first lead system was designed.

6. The process of claim 5, wherein the first lead system comprises one of the following: 1) standard bedside system I; 2) standard EASI system; 3) standard bedside system II; and 4) Dowver EASI system.

7. The process of claim 6, wherein the second lead system comprises one of the following: 1) standard bedside system I; 2) standard EASI system; 3) standard bedside system II; and 4) Dower EASI system.

8. The process of claim 5, wherein the connecting step includes the steps of:
   connecting a first electrode and a second electrode of the first lead system to a first channel of the ECG monitor;
   connecting a third electrode and the second electrode of the first lead system to a second channel of the ECG monitor; and
   connecting the third electrode and a fourth electrode of the first lead system to a third channel of the ECG monitor.

9. The process of claim 1, wherein the first lead system comprises an EASI lead system, and the second lead system comprises a conventional cable having at least four conventional electrodes which provide input to a conventional 3-channel ECG monitor.

10. The process of claim 9, wherein the first electrode is the E electrode, the second electrode is the S electrode, the third electrode is the A electrode, and the fourth electrode is the I electrode of the EASI lead system.

11. The process of claim 1, wherein the first lead system comprises a conventional cable that provides input for a conventional 3-channel ECG monitor, and the second lead system comprises an EASI lead system.

12. The process of claim 11, wherein the first electrode is a left arm electrode, the second electrode is a right arm electrode, the third electrode is a left leg electrode, and the fourth electrode is an exploring electrode of the conventional cable for the conventional 3-channel ECG monitor.

13. A process for sensing and analyzing electrical activity of a human heart, comprising the steps of:
   providing a set of electrodes designed for a first lead system;
   providing an ECG monitor designed to receive output signals from a second lead system that is different from the first lead system, and form output channels consistent with output for which the second lead system was designed;
   connecting output signals from the first lead system electrodes to first, second and third channel inputs for the ECG monitor;
   linearly transforming data provided by the output signals from the first lead system; and
   outputting first, second and third ECG channels which are consistent with output for which the first lead system was designed.

14. The process of claim 13, wherein the connecting step includes the steps of:
   connecting a first electrode and a second electrode of the first lead system to a first channel of the ECG monitor;
   connecting a third electrode and the second electrode of the first lead system to a second channel of the ECG monitor; and
   connecting the third electrode and a fourth electrode of the first lead system to a third channel of the ECG monitor.

15. The process of claim 13, wherein the first lead system comprises an EASI lead system, the second lead system comprises a conventional cable having at least four conventional electrodes which provide input to a conventional 3-channel ECG monitor, and wherein the first electrode is the E electrode, the second electrode is the S electrode, the third electrode is the A electrode, and the fourth electrode is the I electrode of the EASI lead system.

16. The process of claim 13, wherein the first lead system comprises a conventional cable that provides input for a conventional 3-channel ECG monitor, the second lead system comprises an EASI lead system, and wherein the first electrode is a left arm electrode, the second electrode is a right arm electrode, the third electrode is a left leg electrode, and the fourth electrode is an exploring electrode of the conventional cable for the conventional 3-channel ECG monitor.

17. The process of claim 13, wherein the transforming step includes the step of applying an algorithm to the data after the ECG monitor has formed channels.

18. The process of claim 13, wherein the transforming step includes the step of applying an algorithm to the data before the output signals from the first lead system electrodes are fed to the channel inputs for the ECG monitor.

19. A process for sensing and analyzing electrical activity of a human heart, comprising the steps of:

providing a set of electrodes designed for a first lead system taken from the group of 1) standard bedside system I, 2) standard EASI system, 3) standard bedside system II, and 4) Dower EASI system;

providing an ECG monitor designed to receive output signals from a second lead system taken from the group of 1) standard bedside system I, 2) standard EASI system, 3) standard bedside system II, and 4) Dower EASI system, that is different from the first lead system, the ECG monitor being designed to form output channels consistent with output for which the second lead system was designed;

connecting output signals from the first lead system electrodes to first, second and third channel inputs for the ECG monitor;

linearly transforming data provided by the output signals from the first lead system; and outputting first, second and third ECG channels which are consistent with output for which the first lead system was designed.

20. The process of claim 19, wherein the transforming step includes the step of applying an algorithm to the data after the ECG monitor has formed channels.

21. The process of claim 19, wherein the transforming step includes the step of applying an algorithm to the data before the output signals from the first lead system electrodes are fed to the channel inputs for the ECG monitor.

\* \* \* \* \*